US00PP15625P3

(12) United States Plant Patent

Yinger et al.

(10) Patent No.: US PP15,625 P3

(45) Date of Patent: Mar. 8, 2005

(54) *LOROPETALUM CHINENSE* VARIETY *RUBRUM* NAMED 'MELTING POT'

(50) Latin Name: *Loropetalum chinense*
Varietal Denomination: Melting Pot

(75) Inventors: Barry R. Yinger, York Haven, PA (US); Thomas M. Foley, Jr., Katy, TX (US)

(73) Assignee: Hines Nurseries, Inc., Irvine, CA (US)

( * ) Notice: Subject to any disclaimer, the term of this patent is extended or adjusted under 35 U.S.C. 154(b) by 233 days.

(21) Appl. No.: 10/061,087

(22) Filed: Feb. 1, 2002

(65) Prior Publication Data

US 2003/0150030 P1 Aug. 7, 2003

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—W C Haas
(74) *Attorney, Agent, or Firm*—Christie, Parker & Hale, LLP

(57) ABSTRACT

A new plant variety of *Loropetalum chinense* var. *rubrum* characterized by its white flowers and purple colored new foliage which matures to green.

1 Drawing Sheet

Figure 1:
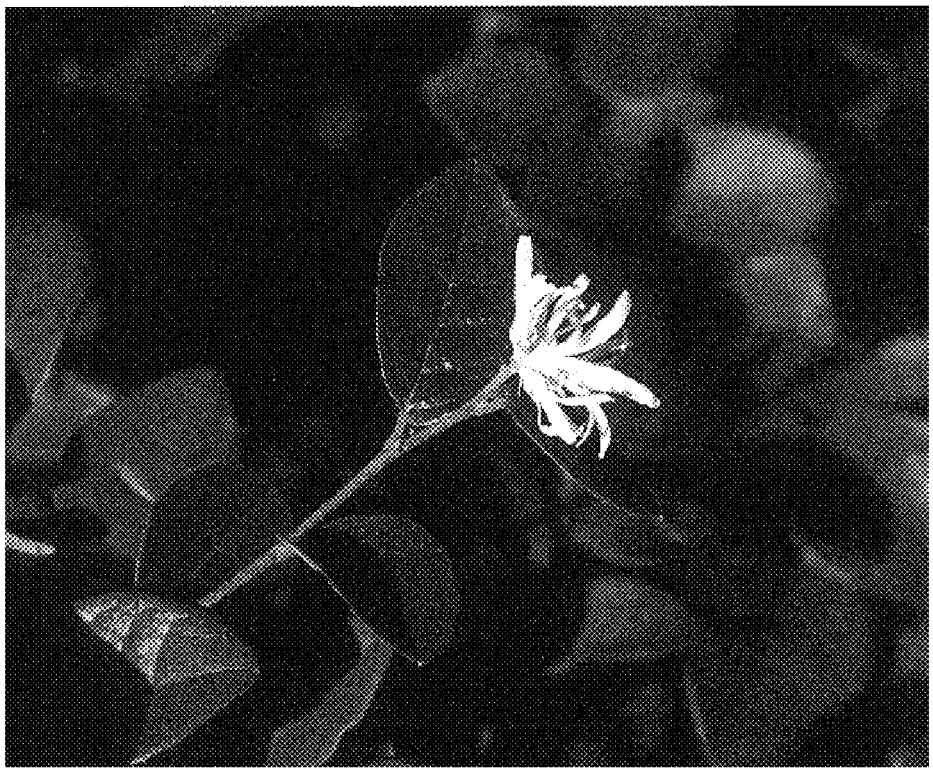

Classification: The present invention relates to a new *Loropetalum chinense* var. *rubrum* Yieh plant.

Variety denomination: The new plant has the varietal denomination 'Melting Pot'.

BACKGROUND OF THE INVENTION

The present invention relates to a new and distinct variety of *Loropetalum chinense* variety *rubrum* Yieh and was discovered a branch sport of *Loropetalum chinense* 'Shibori' (unpatented) in Fulshear, Tex.

The genus *Loropetalum* is included in the family Hamamelidaceae that comprises about 15 genera of shrubs and trees growing in the Northern Hemisphere. *Loropetalum* comprises one species of evergreen shrub or small tree, which possesses desirable ornamental characteristics. *Loropetalum* was first introduced to Europe as an ornamental plant the 1880's, and is believed to have been cultivated in North America since the early 1930's.

*Loropetalum chinense* var. *rubrum* is a native of China, and was first discovered in 1928 in Hunan province. It was rediscovered in the late 1980's and subsequently introduced to the United States. *Loropetalum chinense* var. *rubrum* generally has alternate, ovate leaves to 6 cm long and 3 cm wide. The plant is evergreen or partly evergreen depending on winter temperature. Leaf color ranges from light to dark burgundy, occasionally green, depending on light intensity, cultural conditions and cultivar. Shoots are slender, brown, and densely pubescent, pith is solid. Leaves are generally densely pubescent overall.

Flowers of *Loropetalum chinense* var. *rubrum* are perfect with four (4) strap-like petals which are about 2 cm long and about 0.3 cm wide. Three (3) to six (6) flowers are together in each leaf axil. Pedicel and calyx have a white pubescence. Flower color is pinkish to reddish purple depending on the cultivar. Flowering is heaviest in early spring.

SUMMARY OF THE INVENTION

The new variety was discovered as a branch sport *Loropetalum chinense* 'Shibori' (unpatented), which is a white and pink flowering plant (flowers were pink with white striping). The new variety differs from the parent and other cultivars known to the inventor by having white flowers and purple colored new foliage which matures to green. Asexual reproduction of the new variety by cuttings taken in Fulshear, Tex. and Vacaville, Calif. have confirmed that the distinctive characteristics of the new variety are stable and transmitted to succeeding generations and that the new variety reproduces true to type.

COMPARISON WITH PARENT

'Melting Pot' is distinguished from its parent by its white flowers and purple colored new foliage which matters to green. In contrast, the parent of 'Melting Pot' has flower petals with a pink central stripe and white margins.

BRIEF DESCRIPTION OF ILLUSTRATION

The accompanying photographic illustration shows a plant of the new cultivar as true to color as is reasonably possible to make in an illustration of this character.

FIG. 1 illustrates the distinctive white colored flowers of the new variety.

DETAILED DESCRIPTION OF THE NEW VARIETY

*Loropetalum chinense* var. *rubrum* 'Melting Pot' has not been observed under all possible environmental, cultural, and light conditions. The following observations and descriptions are of plants grown in Fulshear, Tex. and Vacaville, Calif. Phenotypic expression may vary with light intensity, cultural, and environmental conditions. In this description, color references are to The Royal Horticultural Society Colour Chart (2001) and terminology used in the color descriptions herein refers to plate numbers in this color chart. As with many plants in the Hamamelidaceae family, phenotypic characteristics can be dramatically different in terms of growth morphology.

Plant:

*Propagation.*—By vegetative cuttings.

*Age of observed specimen.*—Two-year-old plant in 5-gallon nursery container, grown in Vacaville, Calif.

*Size.*—Grows to approximately 5 ft. tall and about 6 to 8 ft. wide.

*Branching.*—Dense, overall mounding to upright branching habit. Lateral Branches: Multi-branched shrub. Branch Size: Typical branch about 1 m long, pendulous. Branch Diameter: Typical branch about 1 cm in diameter; branch apex is typically about 1 mm or less. Branch Color: Near 166A. Abaxial: Near 182C with midrib venation near 147C.

*Mature leaves.*—Adaxial: Near 147A; occasional mottling occurs, near 144B. Abaxial: Near with mid-rib near 148C.

*Venation.*—Pattern: Pinnate. Color Young foliage Adaxial: Near 137A. Abaxial: Near 147C. Mature foliage Adaxial: Near 144B. Abaxial: Near 148C.

*Petioles.*—Length: Approximately 1 to 3 mm. Diameter: About 0.8 mm. Color Young foliage: Near 145B. Mature foliage: Near 146C.

*Stipule length.*—About 2 to 3 mm.

*Color.*—Near 146C.

*Internodes.*—Between 0.5 to 1.5 cm long.

*Hardiness.*—USDA Zone 7 (0° F. to 7° F.).

*Vigor.*—Moderate. Habit: Young plants exhibit pendulous growth habit. Once plant is established, plant bears obliquely upright branches.

Leaf:

*Arrangement.*—Simple, alternate along the stem.

*Shape.*—Ovate to obovate.

*Apex.*—Acute to obtuse.

*Base.*—Obtuse, occasionally unequal.

*Margin.*—Entire, with stellate hairs.

*Size.*—Young foliage: Length about 1.4 cm; width about 8 mm. Mature foliage: Length about 4.1 cm; width about 2.7 cm.

*Texture.*—Adaxial: Leathery; sparsely pubescent with stellate hairs; lustrous sheen. Abaxial: Leathery; sparsely pubescent with stellate hairs.

*Color.*—Varies with intensity of sunlight and cultural conditions; the following color readings were taken in the month of September 2001 of a 2-year-old plant grown in full sun in Vacaville, Calif.

*Young leaves.*—Adaxial: Near 183A with margins and venation exhibiting color near 137A.

*Pests/diseases.*—No pest or disease problems noted; no resistance to pests and disease noted beyond that which is characteristic of the species.

Flower:

*Habit.*—Globose heads on terminals. Occasionally solitary in the leaf axils.

*Bloom period.*—March through April in Fulshear, Tex. with light repeat blooming throughout the growing season.

*Quantity.*—About 6 to 8 flowers in a globose head.

*Form.*—Perfect, with 4 strap-like petals; forming a loose funnel; petal count can be as high as about 6 to 8.

*Diameter.*—About 1.6 cm.

*Height.*—About 1.4 cm.

*Longevity on plant.*—About 4 to 5 days.

*Fragrance.*—None noted.

*Petals.*—Color Adaxial: Near 155B on the margin with some coloration in the center of the petals near 69A. Abaxial: Near 155B. Arrangement: 4 arising from calyx tube at sepal base, some flowers may have up to 8 petals.

*Shape.*—Linear.

*Margin.*—Entire.

*Apex.*—Retuse.

*Length.*—Between 12 to 15 mm.

*Width.*—Between 2 to 3 mm.

*Texture.*—Smooth.

*Bud.*—Shape: Orbicular. Length: About 3 mm. Diameter: About 2 mm. Color: Near 60B. Rate of opening: About 5 to 7 days.

*Peduncle.*—Length: About 2 mm. Diameter: About 0.5 mm. Color: Near 138D. Aspect: Horizontal to slightly erect in stem axils. Texture: Pubescent.

*Sepals.*—Arrangement: Opposite; 4 per flower; Calyx erect and cruciform. Shape: Ovate with a pointed apex and an entire margin. Color: Near 146C on both surfaces. Length: About 2 mm. Width: About 2 mm. Texture: Pubescent.

Reproductive organs:

*Stamens.*—4.

*Pistils.*—2.

*Pollen.*—Typical Quantity: Minute. Observed Quantity: None observed. Color: Off-white.

*Fruit.*—Type: Loculicidal capsule. Quantity: About 75 to 100 per plant per year. Length: About 5 mm. Diameter: About 6 mm. Color: Near 199A.

I claim:

1. A new plant of *Loropetalum chinense* var. *rubrum* substantially as shown and described.

* * * * *